United States Patent
Bougamont et al.

[11] Patent Number: 5,992,701
[45] Date of Patent: Nov. 30, 1999

[54] DEVICE FOR PACKAGING AND DISPENSING STERILE LIQUID PRODUCTS

[75] Inventors: Jean-Louis Bougamont; Pascal Hennemann, both of Eu, France

[73] Assignee: Sofab, Le Treport, France

[21] Appl. No.: 09/053,773

[22] Filed: Apr. 2, 1998

[30] Foreign Application Priority Data

Apr. 2, 1997 [FR] France ................................. 97 03984

[51] Int. Cl.[6] .............................. B67D 5/58; B65D 47/18
[52] U.S. Cl. ................................ 222/189.06; 222/189.09; 222/420
[58] Field of Search ................... 222/189.06, 189.09, 222/420, 421

[56] References Cited

U.S. PATENT DOCUMENTS

| | | |
|---|---|---|
| 3,149,758 | 9/1964 | Bush et al. . |
| 4,463,880 | 8/1984 | Kramer et al. ............... 222/189 |
| 5,105,993 | 4/1992 | La Haye et al. ............. 222/189 |
| 5,219,101 | 6/1993 | Matkovich et al. ......... 222/189 |
| 5,490,938 | 2/1996 | Sawan et al. ............... 210/651 |
| 5,611,464 | 3/1997 | Tsao et al. ................ 222/189.06 |
| 5,688,397 | 11/1997 | Malmborg ................... 210/136 |

FOREIGN PATENT DOCUMENTS

| | | |
|---|---|---|
| 0 332 480 | 9/1989 | European Pat. Off. . |
| 0 459 498 | 12/1991 | European Pat. Off. . |
| 0 602 019 | 6/1994 | European Pat. Off. . |
| 823.360 | 1/1938 | France . |
| 823360 | 1/1938 | France . |
| 2 340 870 | 9/1977 | France . |
| 2 422 569 | 11/1979 | France . |
| 2 478 589 | 9/1981 | France . |
| 2478589 | 9/1981 | France . |

*Primary Examiner*—Joseph A. Kaufman
*Assistant Examiner*—Keats Quinalty
*Attorney, Agent, or Firm*—Bacon & Thomas PLLC

[57] ABSTRACT

A device for packaging and dispensing a sterile liquid product. The device comprises a reservoir on which a nozzle is mounted. The nozzle is provided with an inner conduit which has an upstream end communicating with the reservoir and a downstream end opening to the outside via an evacuation orifice. The inner conduit is at last partially obturated by an insert of selective porosity which allows both a metered flow of the product to the outside and a filtration of air sucked towards the inside, stopping biological polluting and/or contaminating agents.

19 Claims, 4 Drawing Sheets

DEVICE FOR PACKAGING AND DISPENSING STERILE LIQUID PRODUCTS

FIELD OF THE INVENTION

The present invention relates to a device for packaging and dispensing sterile liquid products and more particularly pharmaceutical products for ophthalmic use.

BACKGROUND OF THE INVENTION

Devices of this type already exist, such as the one forming the subject matter of Patent Application FR 96 00120.

These devices comprise in particular a reservoir of product on which is mounted a nozzle which is provided with an inner conduit communicating at its upstream end with the reservoir and opening at its downstream end to the outside via an evacuation orifice. The inner conduit is generally hermetically obturated, on the one hand, by a valve at the level of the evacuation orifice and, on the other hand, by means of an elastically deformable, inner sealing lip.

However, these obturation means, which are mobile or deformable, are complex, and both manufacture and assembly thereof on the device are delicate and expensive operations.

In addition, these devices do not guarantee drop-by-drop dispensing, which constitutes a major handicap for products whose posology may be strictly prescribed.

In addition, certain of these devices function without air intake, which brings about a deformation of the reservoir and requires a supple structure. Finally, others cannot ensure filtration of the gaseous flow sucked towards the reservoir during air intake consecutive to the delivery of a dose of product. This results in a considerable risk of contamination or pollution of the product.

It is an object of the present invention to solve these technical problems satisfactorily.

SUMMARY OF THE INVENTION

This object is attained, according to the invention, by means of a device for packaging and dispensing a sterile liquid product, of the type comprising a reservoir on which is mounted a nozzle provided with an inner conduit communicating with said reservoir at its upstream end and opening to the outside at its downstream end via an evacuation orifice, characterized in that said nozzle comprises, on the one hand, an insert of selective porosity obstructing the inner conduit at least partially and allowing both a metered flow of the product towards the outside and a filtration of the air sucked towards the inside, stopping biologically polluting and/or contaminating agents, said insert comprising a finger which is inserted in the evacuation orifice, whose end projects to the outside, and, on the other hand, a cap covering said nozzle and bearing an element for hermetically obturating said evacuation orifice.

According to a particular embodiment, said obturation element is constituted by an inner peripheral lip adapted to abut around the evacuation orifice via the outside, when the cap is placed on the nozzle.

According to a variant embodiment, said cap comprises a locking member cooperating by clipping with a retaining member arranged on the nozzle.

According to another variant, said cap comprises stiffening elements abutting on the nozzle.

According to an advantageous characteristic, said insert presents a profile adapted to be housed in the downstream end of said conduit.

According to another embodiment, said nozzle comprises a valve whose seat is formed by the edges of the evacuation orifice, and which is associated with elastic return means borne by said insert.

According to a variant, said elastic return means are constituted by an elastically deformable ring retained by its peripheral edge beneath a shoulder of the nozzle.

According to a further characteristic, the device is made at least partially of a material containing a bactericidal and/or antiseptic chemical agent.

According to other characteristics, the porosity of said insert is included between 40% and 60% and the diameter of the pores is preferably included between 5 and 10 μm.

The porosity of the insert may be non-uniform and define in its mass channels for the preferential flow of the product.

The device of the present invention ensures both a precise and reproducible dosage and a protection against bacteria of the product, by using simple technical means.

Tightness of the device is completed and reinforced by the action of the cap.

In addition, the porous insert is a simple, reliable and economical constituent which has a synergetic action with the other constituents of the device to ensure jointly the regulation of the flow of product, the filtration of the sucked air and the necessary tightness of the device.

BRIEF DESCRIPTION OF THE DRAWINGS

The invention will be more readily understood on reading the following description with reference to the accompanying drawings, in which.

DESCRIPTION OF PREFERRED EMBODIMENTS

Figure 1:
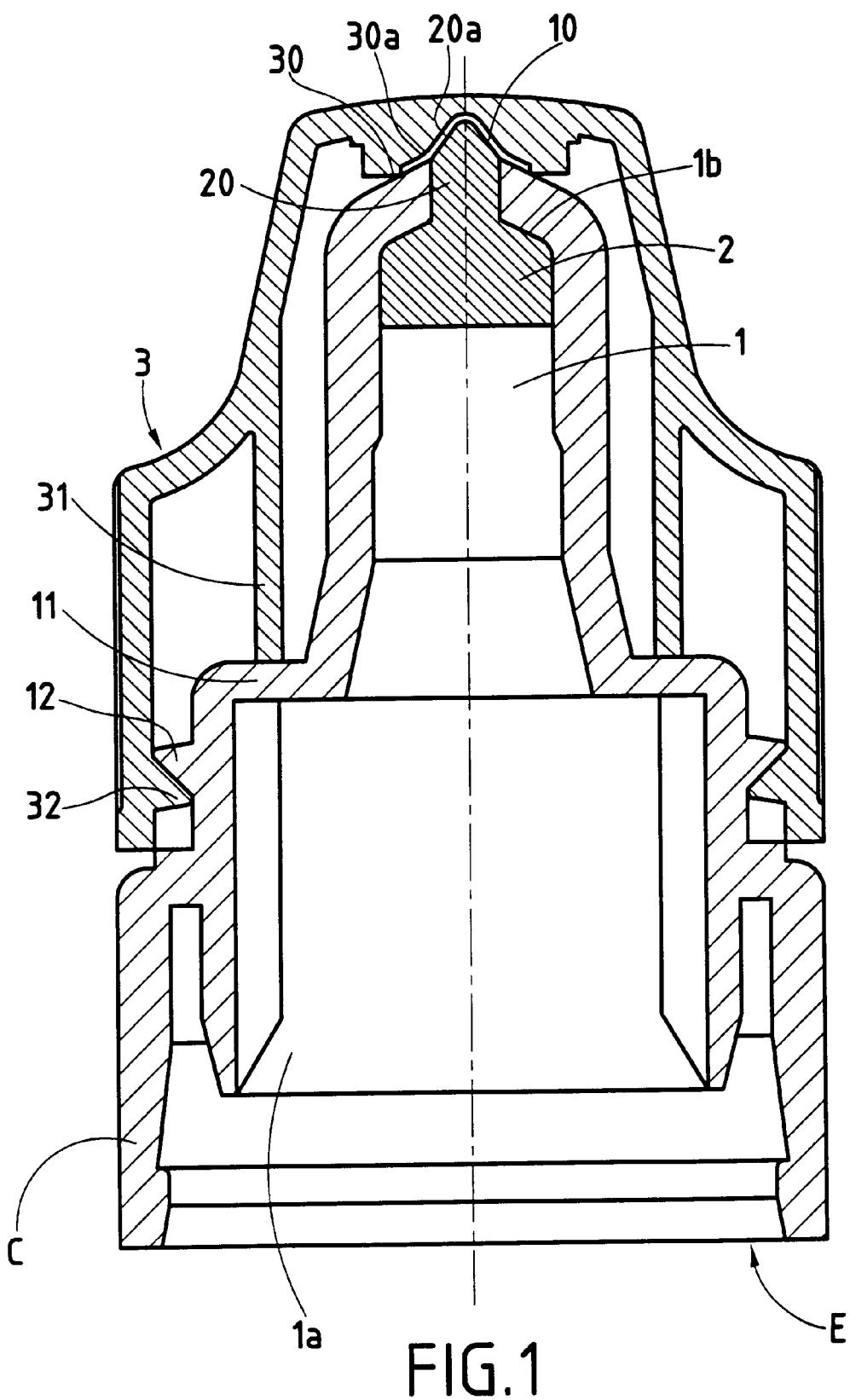
FIG. 1 shows a view in section of a first embodiment of the device of the invention.
Figure 2:
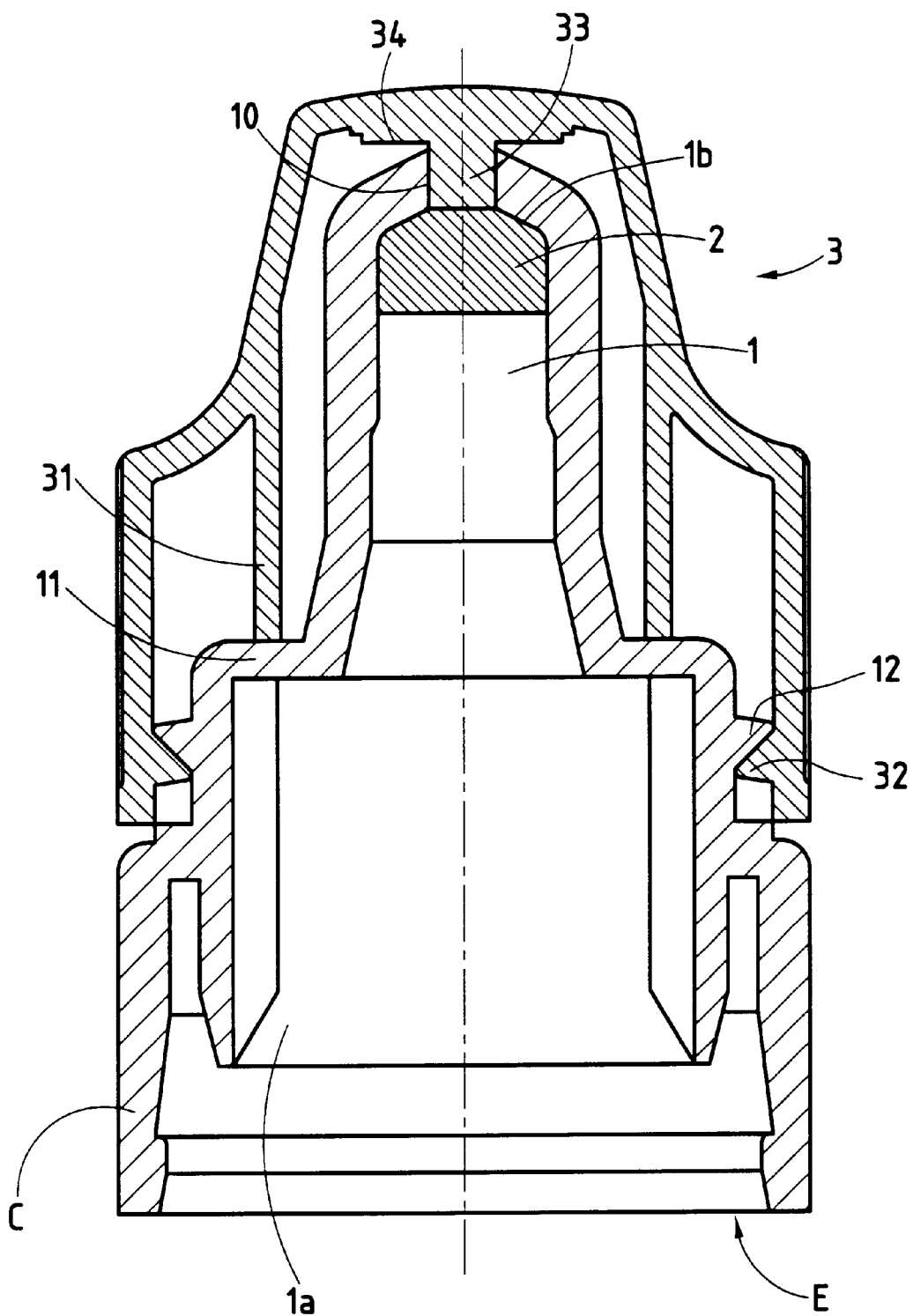
FIG. 2 shows a view in section of a second embodiment of the device of the invention.
Figure 3:
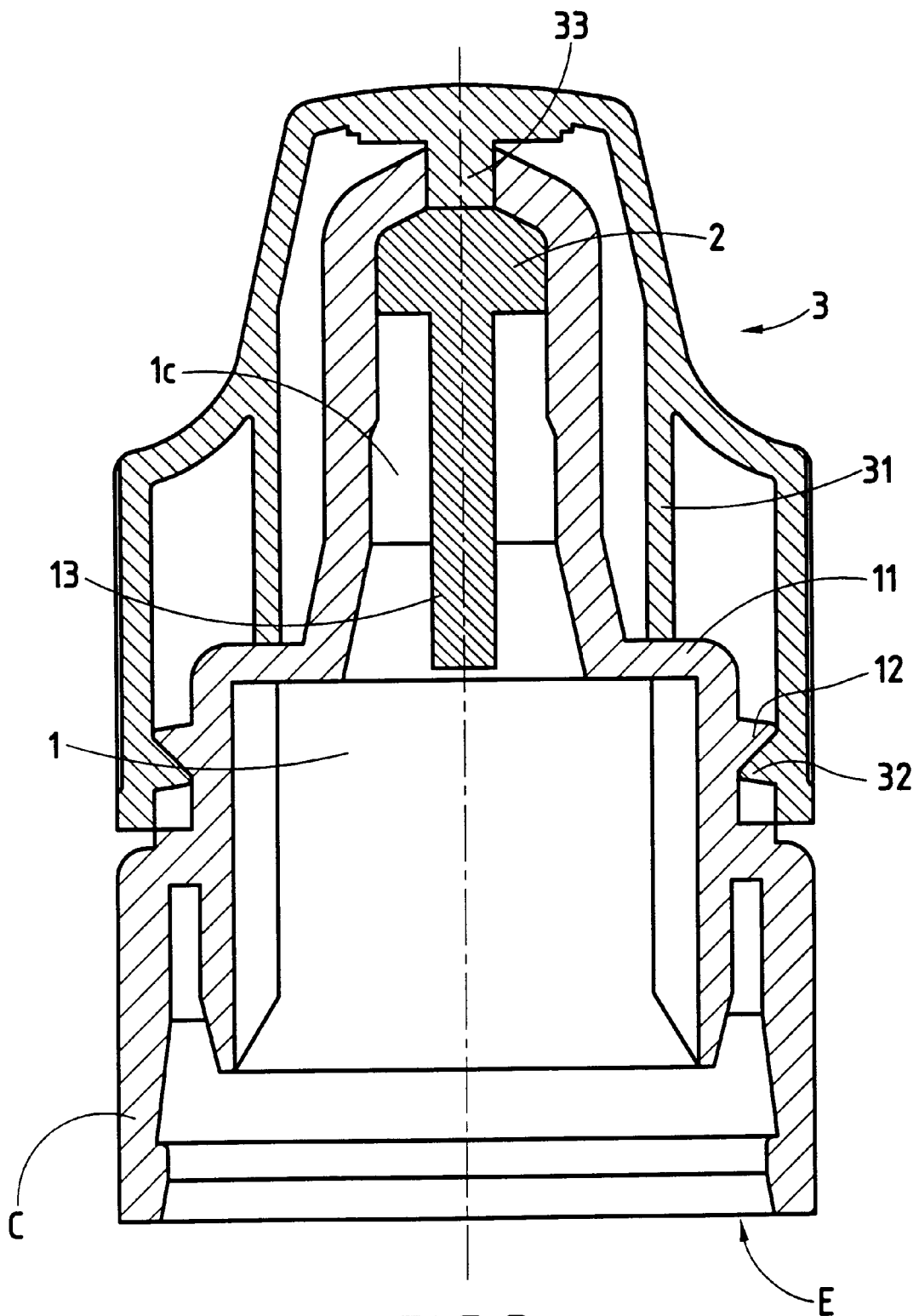
FIG. 3 shows a view in section of a variant embodiment of the device of FIG. 2.
Figure 4:
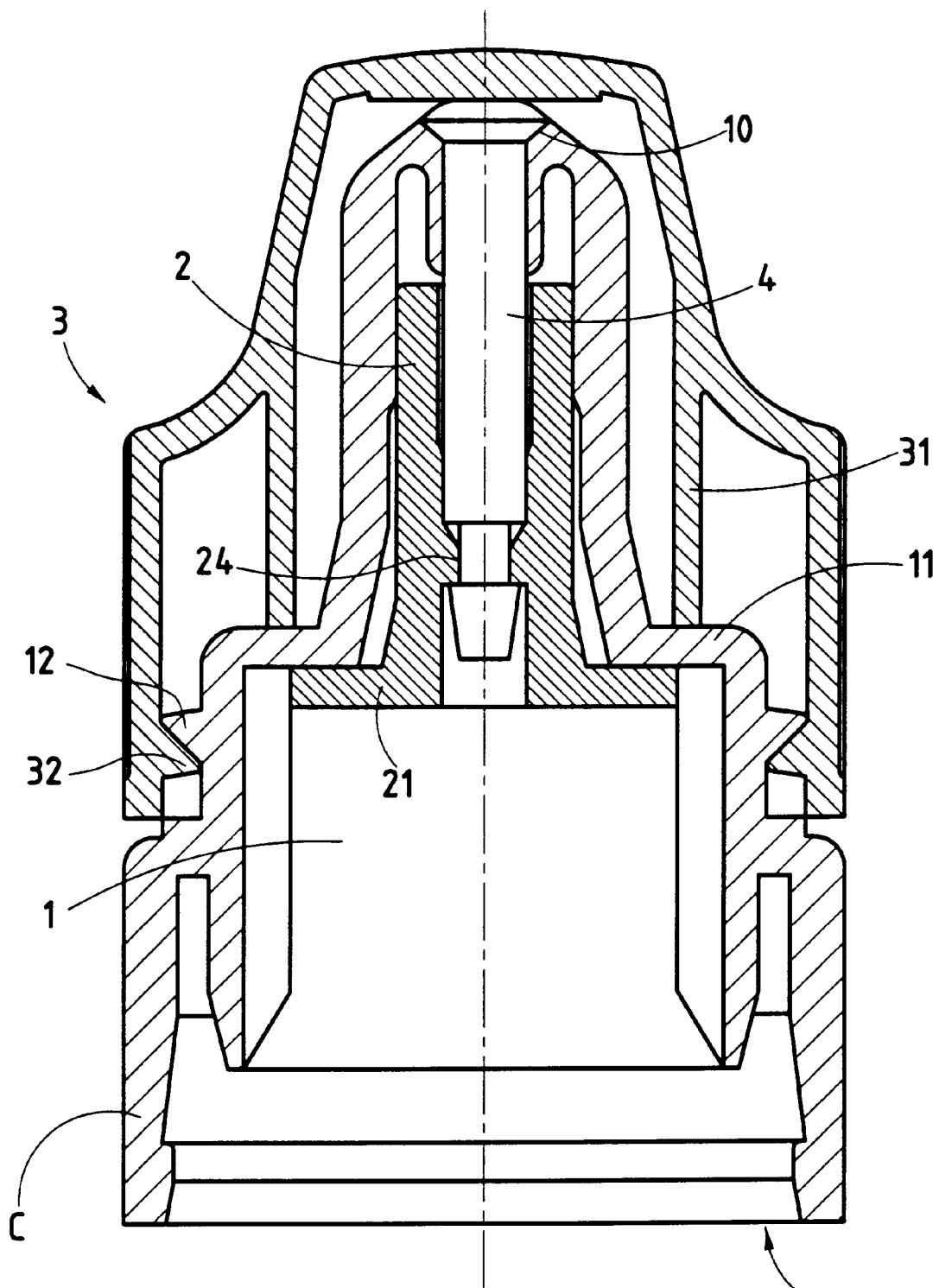
FIG. 4 shows a view in section of a third embodiment of the device of the invention.

Referring now to the drawings, the device shown in FIG. 1, like those shown in FIGS. 2 to 4, is more particularly intended for packaging and dispensing a sterile liquid product.

This device comprises a reservoir (not shown) on which is mounted a nozzle E.

Nozzle E is provided with a flange C for connection to the reservoir and with an inner conduit 1 communicating at its upstream end 1a with the reservoir and opening to the outside by its downstream end 1b, via an evacuation orifice 10.

Conduit 1 is obstructed at least partially by an insert 2 made of a material of selective porosity.

More precisely, this porosity is such that insert 2 ensures, on the one hand, a dosage of the product by slowing down its flowrate towards the outside, when the reservoir is placed under pressure and, on the other hand, a filtration of the air sucked towards the inside when the internal pressure of the reservoir returns to atmospheric pressure.

Air intake thus occurs, stopping the biological polluting and/or contaminating agents.

In FIG. 1, the insert 2 presents a profile adapted to be housed in the downstream end 1b of the conduit 1 with a slight radial tightening or a weak compression, occupying all the free section.

Consequently, the total flow of liquid product has to traverse the insert 2, this regulating the flowrate. Transfer is effected under pressure, firstly by impregnation of the insert through the pores, then by release of the product.

The porosity of the insert 2 is preferably included between 40% and 60% with a pore diameter included between 5 and 10 $\mu$m. This makes it possible to produce both a drop-by-drop dosage in one direction and a stoppage or trapping of the principal contaminating agents in the other direction.

The insert is possibly impregnated with or made at least partially of a material having a bactericidal activity (for example an oligodynamic substance based on silver).

In the embodiment of FIG. 1, the insert 2 comprises a finger 20 which is inserted in the evacuation orifice 10 with a slight radial tightening. The end 20a of the finger 20 projects to the outside with an ogival profile promoting the formation of drops of product and making it possible to calibrate the volume of the drops preferably between 25 $\mu$l and 50 $\mu$l.

The device of the invention further comprises a cap 3 intended to cover at least the end of the nozzle E.

Cap 3 bears an element for hermetically obturating the evacuation orifice 10.

In the embodiment of FIG. 1, this element is constituted by a peripheral lip 30 formed on the inner wall of the cap 3 and which is adapted to abut around the orifice 10 via the outside when the cap 3 is placed on the nozzle E.

The lip 30 is relatively rigid and borders a cavity 30a, formed on the inner wall of the cap 3, in which the ogival end 20a of the finger 20 of the insert 2 is housed.

Where the end 20a of the finger 20 is adjusted with slight clearance to the dimensions of the cavity 30a, the opposite mutual surfaces define a dead space ensuring anti-bacterial protection.

The cap 3 also comprises a locking member 32 cooperating by clipping with a retaining member 12 formed on the nozzle E.

The position and geometry of the locking (32) and retaining (12) members are determined so as to ensure tight abutment of the lip 30 around the orifice 10 and therefore a hermetic assembly of the cap 3 on the nozzle E.

The cap 3 further comprises stiffening elements 31 in the form of fins or a cylinder abutting on a shoulder 11 of the nozzle E.

With a view to reinforcing biological protection of the product, it is possibly provided to make the device (nozzle E and/or insert 2 and/or cap 3) of a plastic material containing a bactericidal and/or antiseptic chemical agent.

In the embodiment of FIG. 2, the obturation element borne by the cap 3 is constituted by an inner stud 33 adapted to be introduced in the evacuation orifice 10 when the cap 3 is placed on the nozzle E.

The inner end of the stud 33 comes into contact with the insert 2 formed by a piece housed in the downstream end 1b of the conduit 1 and which, after the cap 3 has been removed, leaves orifice 10 totally free for the flow of the product.

Bearing of the stud 33 against the insert 2 is limited by a transverse face 34 on the inner wall of the cap 3, which abuts on the outside end edge of the orifice 10.

FIG. 3 shows a variant of the device of FIG. 2 in which the insert 2 extends inside the conduit 1 towards the reservoir, via a rod 13 of the same material.

Rod 13 presents a smaller diameter than the internal diameter of the conduit 1, thus forming a coaxial annular cavity 1c around said rod. Rod 13 forms a wick conducting the liquid product up to the heart of the insert 2.

In accordance with another variant (not shown), rod 13 may even extend over the whole length of the nozzle E and reservoir until it is immersed in the product.

According to another embodiment (not shown), the porosity in the insert is non-uniform, this defining in its mass channels for the preferential flow and/or circulation of the product.

In the embodiment of FIG. 4, the nozzle E comprises a valve 4 whose seat is formed by the edges of the evacuation orifice 10. The valve 4 is associated with elastic return means, here in the form of a ring 21, borne by the insert 2 and made of an elastically deformable material, possibly in one piece with the body of the insert 2.

The ring 21 is retained by its peripheral edge beneath the inner wall of the shoulder 11 of nozzle E.

The valve 4 is rendered fast with the insert 2 by means of a flange 24.

What is claimed is:

1. A device for packaging and dispensing a sterile fluid product, comprising:

a reservoir defining an inside and an outside relative thereto; and a nozzle mounted on said reservoir and provided with an inner conduit, said inner conduit having an upstream end communicating with said reservoir and a downstream end opening to the outside via an evacuation orifice, said nozzle comprising an insert of selective porosity which at least partially obstructs said inner conduit and which allows both a metered flow of the product towards the outside and a filtration of air sucked towards the inside, said filtration stopping biologically polluting and/or contaminating agents, said insert comprising a finger which is inserted in said evacuation orifice and has an end projecting to the outside; and a cap removably covering said nozzle, said cap bearing an element which hermetically obturates said evacuation orifice when said cap is covering said nozzle.

2. The device according to claim 1 wherein said obturation element is an inner peripheral lip adapted to abut around said evacuation orifice via the outside when said cap is covering said nozzle.

3. The device according to claim 1 wherein said cap comprises a locking member which cooperates with a retaining member arranged on said nozzle.

4. The device according to claim 1 wherein said cap comprises stiffening elements which abut on said nozzle when said cap is covering said nozzle.

5. The device according to claim 1 wherein said insert presents a profile adapted to be housed in said downstream end of said conduit.

6. The device according to claim 1 wherein the device is made at least partially of a material containing a bactericidal and/or antiseptic chemical agent.

7. The device according to claim 1 wherein the porosity of said insert is between 40% and 60%.

8. The device according to claim 1 wherein said insert has pores with diameters between 5 micrometers and 10 micrometers.

9. The device according to claim 1 wherein said porosity of said insert is non-uniform and defines channels for preferential flow of the product.

10. The device according to claim 1 wherein said porosity of said insert is non-uniform and defines channels for preferential flow of the product.

11. A device for packaging and dispensing a sterile fluid product, comprising:

a reservoir defining an inside and an outside relative thereto;

a nozzle mounted on said reservoir and provided with an inner conduit, said inner conduit having an upstream end communicating with said reservoir and a downstream end opening to the outside via an evacuation orifice, said nozzle comprising an insert of selective porosity which at least partially obstructs said inner conduit and which allows both a metered flow of the product towards the outside and a filtration of air sucked towards the inside, said filtration stopping biologically polluting and/or contaminating agents, said nozzle further comprising a valve with a seat formed by edges of said evacuation orifice, said valve being associated with an elastic return means which is borne by said insert; and a cap removably covering said nozzle, said cap bearing an element which hermetically obturates said evacuation orifice when said cap is covering said nozzle.

12. The device according to claim 11 wherein said elastic return means is an elastically deformable ring having a peripheral edge which is retained beneath a shoulder of said nozzle.

13. The device according to claim 11 wherein said obturation element is an inner peripheral lip adapted to abut around said evacuation orifice via the outside when said cap is covering said nozzle.

14. The device according to claim 11 wherein said cap comprises a locking member which cooperates with a retaining member arranged on said nozzle.

15. The device according to claim 11 wherein said cap comprises stiffening elements which abut on said nozzle when said cap is covering said nozzle.

16. The device according to claim 11 wherein said insert presents a profile adapted to be housed in said downstream end of said conduit.

17. The device according to claim 11 wherein the device is made at least partially of a material containing a bactericidal and/or antiseptic chemical agent.

18. The device according to claim 11 wherein the porosity of said insert is between 40% and 60%.

19. The device according to claim 11 wherein said insert has pores with diameters between 5 micrometers and 10 micrometers.

* * * * *